United States Patent [19]
Volkonsky et al.

[11] Patent Number: 5,705,195
[45] Date of Patent: Jan. 6, 1998

[54] MAGNETICALLY RESPONSIVE COMPOSITION FOR CARRYING BIOLOGICALLY ACTIVE SUBSTANCES AND METHODS OF PRODUCTION AND USE

[75] Inventors: Viktor A. Volkonsky; Sergei D. Dvukhsherstnov; Sergei V. Chernyakov, all of Moscow, Russian Federation

[73] Assignee: Magnetic Delivered Therapeutics, Inc., Boulder, Colo.

[21] Appl. No.: 480,195

[22] Filed: Jun. 7, 1995

Related U.S. Application Data

[63] Continuation of Ser. No. 188,062, Jan. 26, 1994, Pat. No. 5,549,915, which is a continuation-in-part of Ser. No. 011,363, Jan. 29, 1993, abandoned.

[51] Int. Cl.$^6$ .................. A61K 9/16; A61K 9/50
[52] U.S. Cl. ............... 424/490; 424/463; 424/1.29; 424/489
[58] Field of Search ................. 424/490, 489, 424/1.29, 463

[56] References Cited

U.S. PATENT DOCUMENTS

| | | | |
|---|---|---|---|
| 3,718,594 | 2/1973 | Miller | 252/62.1 |
| 4,106,488 | 8/1978 | Gordon | 424/85 |
| 4,247,406 | 1/1981 | Widder et al. | 252/62.53 |
| 4,331,654 | 5/1982 | Morris | 252/62.1 |
| 4,345,588 | 8/1982 | Widder et al. | 128/260 |
| 4,501,726 | 2/1985 | Schroder et al. | 604/890 |
| 4,652,257 | 3/1987 | Chang | 604/52 |
| 4,690,130 | 9/1987 | Mirell | 424/85 |
| 4,818,614 | 4/1989 | Fukui et al. | 428/403 |
| 4,849,209 | 7/1989 | Lieberman et al. | 534/10 |
| 4,871,716 | 10/1989 | Longo et al. | 424/491 |
| 4,963,360 | 10/1990 | Argaud | 424/443 |

FOREIGN PATENT DOCUMENTS 0451299  10/1991  European Pat. Off.

OTHER PUBLICATIONS

Imshennik, et al., "The formation of magnetic iron clusters on activated carbon", Chemical Abstracts Service, Columbis, Ohio; Hyperfine Interact. 57(1–4), 1875–81, 1990; Coden: Hyindn; ISSN: 0304–3843, 1990.
Patent Abstracts of Japan, vol. 008 No. 241 (C–250), 6 Nov 1984; and JP A–59 122429, Jul. 14, 1984.

*Primary Examiner*—Thurman K. Page
*Assistant Examiner*—William E. Benston, Jr.
*Attorney, Agent, or Firm*—Fish & Richardson P.C.

[57] ABSTRACT

A magnetically controllable, or guided, carrier composition and methods of use and production are disclosed, the composition for carrying biologically active substances to a treatment zone in a body under control of a magnetic field. The composition comprises composite, volume-compounded ferrocarbon particles of 0.2 to 5.0 μm in size, and preferably between 1.0 and 4.0 μm, containing 1.0 to 95.0% by volume of carbon, and preferably between about 20 and 50%. The particles are produced by a joint deformation of a mechanical mixture of iron and carbon powders. The obtained particles are placed in a solution of a biologically active substance to absorb the substance onto the particles. The combination is administered in suspension.

13 Claims, 4 Drawing Sheets

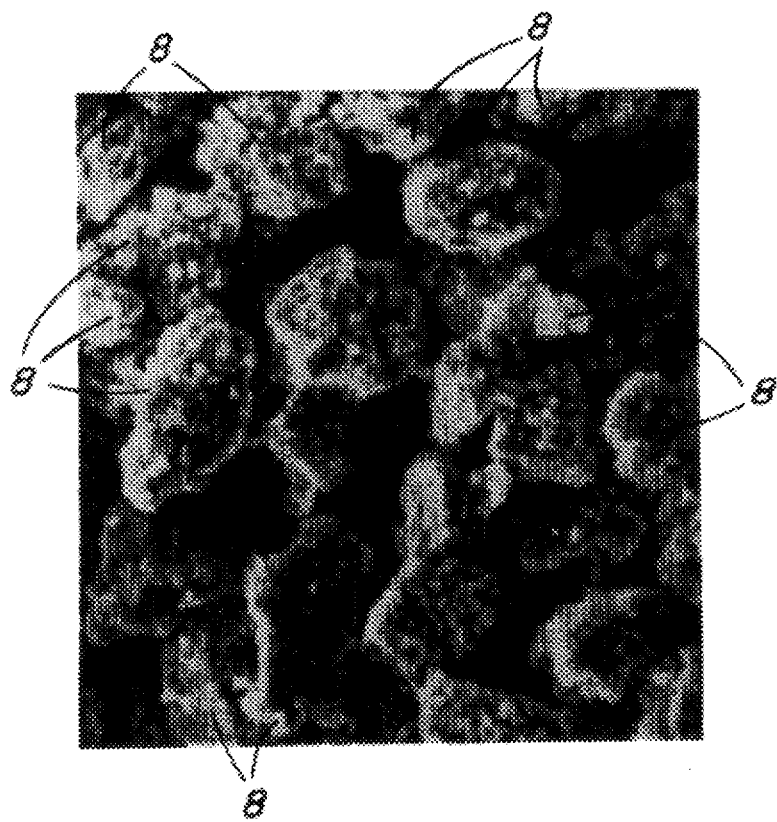
Fig_1
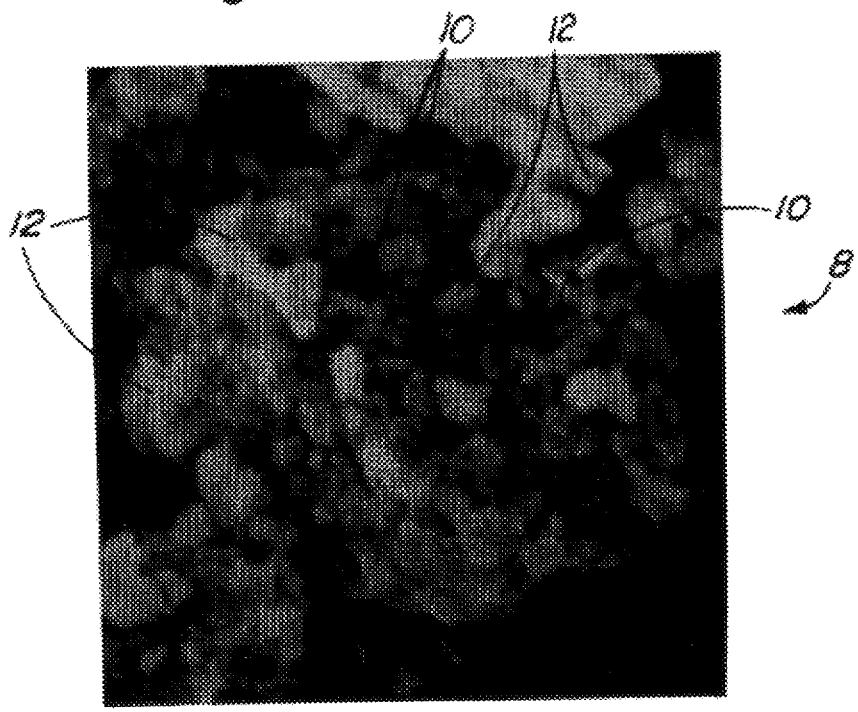
Fig_2a

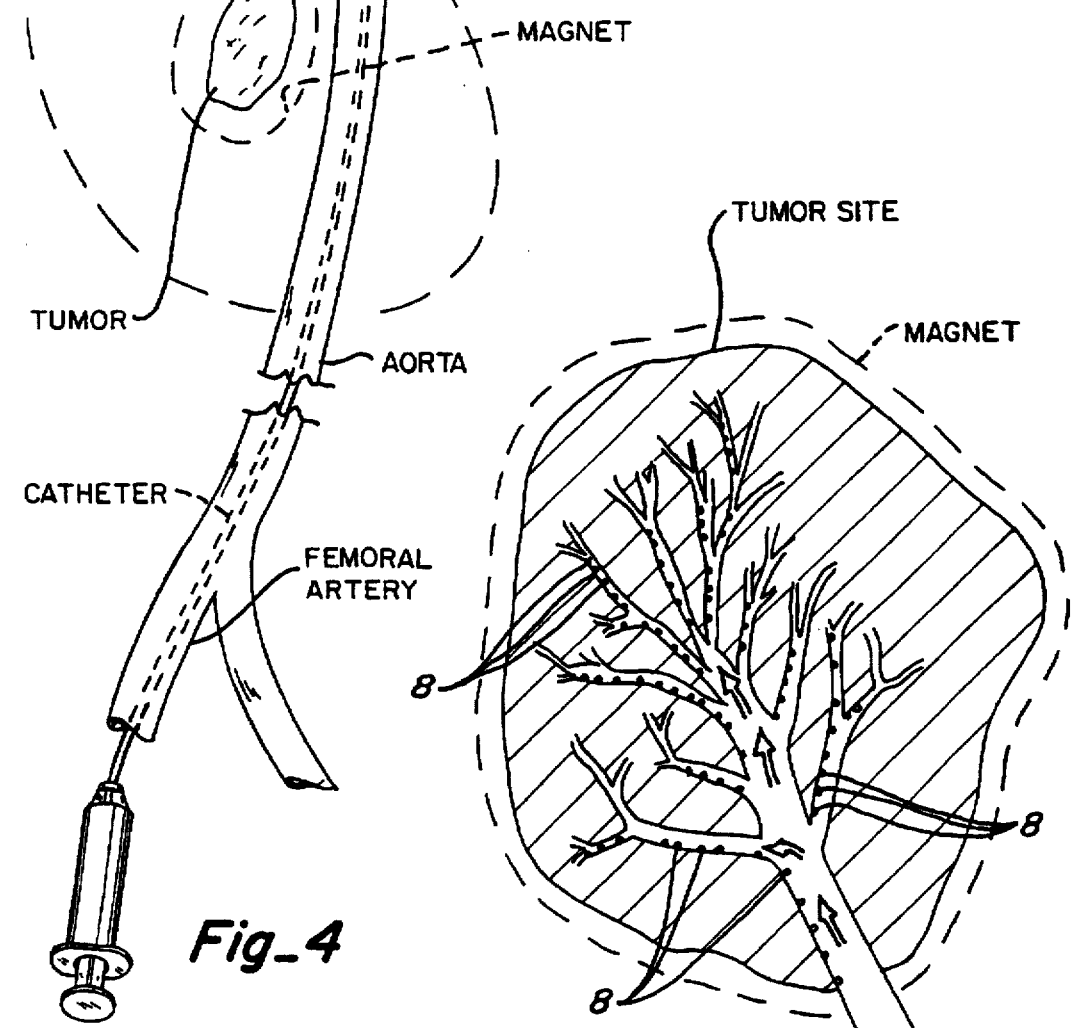
Fig_4
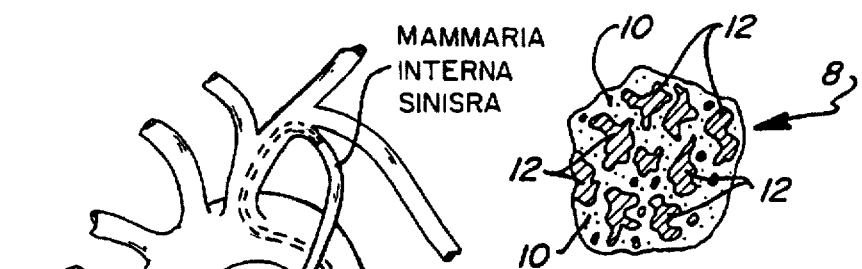
Fig_2b
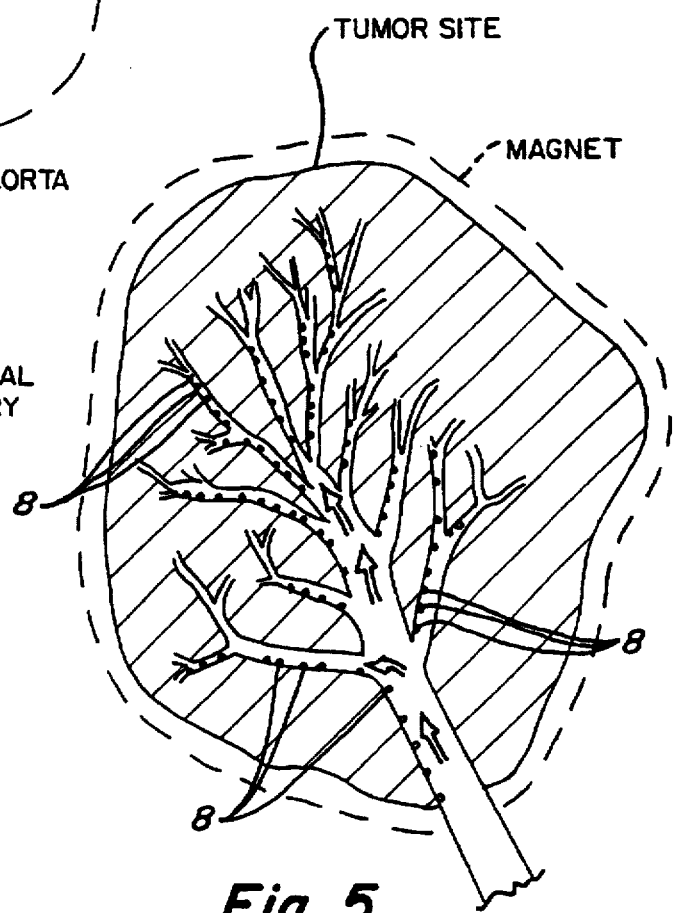
Fig_5

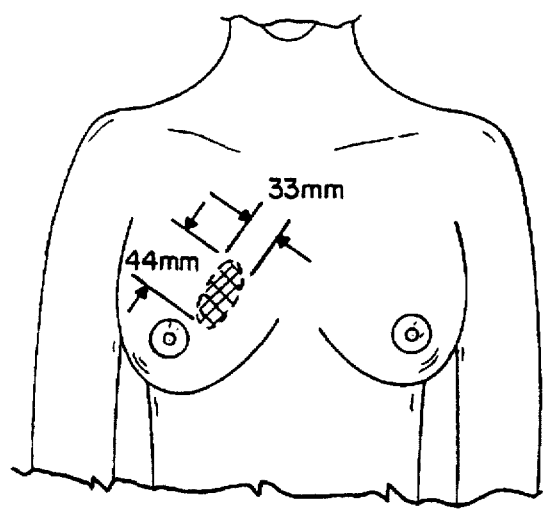
Fig_3a
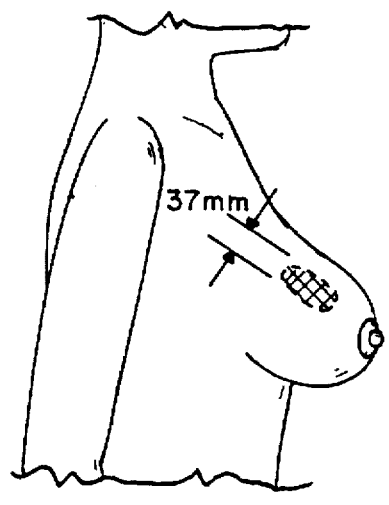
Fig_3b
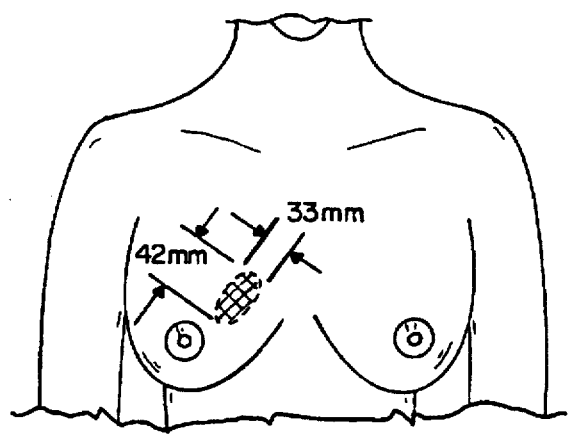
Fig_3c
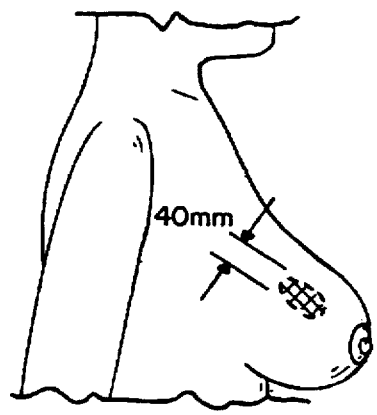
Fig_3d
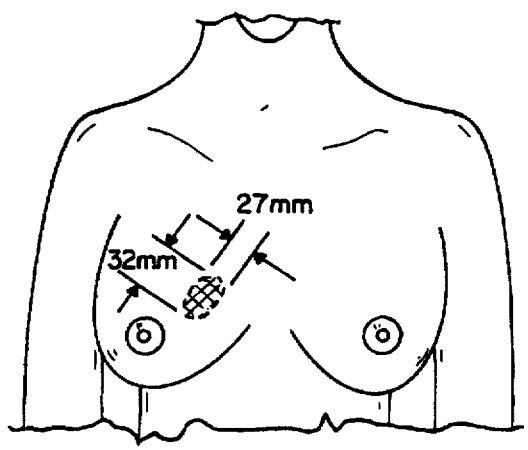
Fig_3e
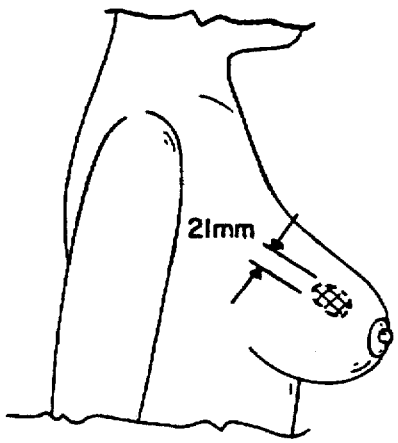
Fig_3f

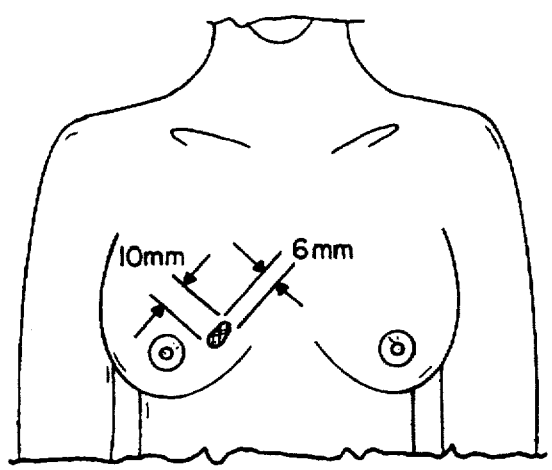 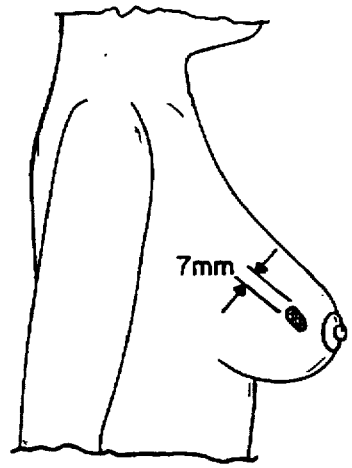
Fig_3g    Fig_3h

MAGNETICALLY RESPONSIVE COMPOSITION FOR CARRYING BIOLOGICALLY ACTIVE SUBSTANCES AND METHODS OF PRODUCTION AND USE

RELATED APPLICATION

This is a continuation of application Ser. No. 08/188,062, filed Jan. 26, 1994, now U.S. Pat. No. 5,549,915 which is a continuation-in-part of Ser. No. 08/011,363, filed Jan. 29, 1993 now abn.

FIELD OF THE INVENTION

This invention relates to compositions and methods for delivery of medicament to a selected location in a body, and, more particularly, relates to carriers for drugs, their methods of production and use, which provide for targeted magnetic transport of the drugs and the maintenance of them in a predetermined place, the aim being exercise of local influence on pathological structures in the body.

BACKGROUND OF THE INVENTION

Metallic carrier compositions used in the treatment of various disorders have been heretofore suggested and/or utilized (see, for example, U.S. Pat. Nos. 4,849,209 and 4,106,488), and have included such compositions which are guided or controlled in a body in response to external application of a magnetic field (see, for example, U.S. Pat. Nos. 4,501,726, 4,652,257 and 4,690,130). Such compositions have not always proven practical and/or entirely effective, however, for example lacking adequate capacity for carriage of the desired biologically active agent to the treatment site, having less than desirable magnetic susceptibility and/or being difficult to manufacture, store and/or use.

For example, one such known composition, deliverable by way of intravascular injection, includes microspheres made up of a ferromagnetic component covered with a biocompatible polymer (albumin, gelatine, polisaccharides) which also contains a drug (Driscol C. F. et al. Prog. Am. Assoc. Cancer Res., 1980, p. 261).

It is possible to produce albumen microspheres up to 3.0 mcmm in size containing a magnetic material (magnetite $Fe_3O_4$) and anti-tumoral antibiotic doxorubine (Widder K. et al. J. Pharm. Sci. 1979, v. 68, No. 1, p. 79–82). Such microspheres are produced through thermal and/or chemical denaturation of albumin in an emulsion (water in oil), with the input phase containing a magnetite suspension in a medicinal solution. Similar technique has been used to produce magnetically controlled, or guided, microcapsules covered with ethylcellulose containing antibiotic mitimicine (Fujimoto S. et al., Cancer, 1985, v. 56, (10), p. 2404–2410).

Another method is to produce magnetically controlled liposomes 200 to 800 nm in size carrying preparations which can dissolve atherosclerotic formations. This method is based on the ability of phospholipides to create closed membrane structures in the presence of water (Gregoriadis G., Ryman B. E., Biochem. J., 1971, v. 124, p. 58).

The above compositions have a number of serious shortcomings which make their practical medical use difficult, including requirement of extremely high flux density magnetic fields for their control, the lack of technical ability to produce standard magnetically controlled microspheres or liposomes on an industrial scale and the inability to consistently sterilize and store such compositions without changing their designed properties.

To overcome these shortcomings a method for producing magnetically controlled dispersion has been suggested (See European Patent Office Publication No. 0 451 299 A1, by Kholodov L. E., Volkonsky V. A., Kolesnik N. F., et al.), the essence of which is that ferrocarbon particles be used as a ferromagnetic material. The ferrocarbon particles are produced by heating iron powder made up of particles 100 to 500 µm at temperatures of 800° to 1200° C. in an oxygen containing atmosphere, with subsequent treatment by carbon monoxide at 400° to 700° C. until carbon particles in an amount of 10 to 90% mass begin emerging on the surface. A biologically active substance is then absorbed on them.

This technology of manufacturing ferrocarbon particles is rather complicated and requires a lot of power. The process is accompanied by oxidation of the ferromagnetic component due to the synthesis of ferrocarbon particles at a high temperature in an oxygen containing atmosphere which dramatically decreases magnetic susceptibility of the dispersion obtained in this way (a 2 times decrease on the average as compared with metallic iron). The magnetically controlled dispersion produced by this technology has relatively low absorption capacity (2.0 to 2.5% of the mass of a ferromagnetic particle is the typical upper limit of absorption of a biologically active substance on such particles).

Furthermore, the magnetically controlled particle itself has a ferromagnetic component of a spheroidal form with a thread-like carbon chain extending from it. The overall size of such a composite particle is less than 2.0 µm. Such structure of the ferrocarbon particle predetermines its relatively low absorption capacity, and also leads to breaking of the fragile thread-like chains of carbon from the ferromagnetic component during storage and transportation as well as difficulties during packaging because of its looseness.

Further development in this field could thus still be utilized.

SUMMARY OF THE INVENTION

This invention provides a magnetically responsive composition for carrying biologically active substances (any soluted substance can be carried, many of which have been heretofore suggested, for example, without limitation, alkylating agents, antimetabolites, antitumor antibiotic chemotherapy agents or combinations thereof, and other therapeutic agents and drugs such as systemic toxicity inhibitors, hydracortosone or the like), and methods of production and use thereof, wherein the above-mentioned shortcomings are eliminated.

The aim of this invention is to improve some parameters of magnetically controlled compositions used for the targeted transport of biologically active substances, including increasing relative absorption capacity, increasing magnetic susceptibility, intensifying therapeutic effect and easiness of use, as well as simplifying the technology of manufacturing the magnetically controlled composition and ensuring its guaranteed long storage without changing its desired characteristics.

This is achieved by using composite, volume-compounded ferrocarbon particles as a magnetically susceptible material for a magnetically controlled composition. These particles have a size of 0.2 to 5.0 µm (and preferably from 1.0 to 4.0 µm) and contain from 1.0 to 95.0% (by volume) of carbon relatively uniformly distributed throughout the volume of a composite particle and strongly connected with iron, the particles being obtained by a joint deformation of a mechanical mixture of iron and carbon powders.

The composition utilized for localized in vivo treatment of disease includes a carrier including particles between about 1 μm and 4 μm in size, each particle including carbon and iron with the carbon distributed throughout the volume of the particle, and a biologically active substance selected for its efficacy in treating the disease absorbed on the particles.

The method of producing the composition includes the step of jointly deforming a mechanical mixture of iron and carbon powders for a time sufficient to bind the powders into particles less than 5 μm in size, each particle including carbon and iron with the carbon distributed throughout the volume of each of the particles. The particles are preferably separated to select particles of a size of between about 1 μm and 4 μm, after which a biologically active substance can be absorbed onto the selected particles.

The methods of use include methods for localized in vivo treatment of disease comprising providing a magnetically responsive ferrocarbon carrier (such as the carrier of this invention) having a biologically active substance selected for its efficacy in treating the disease absorbed thereon, injecting the carrier into the body of a patient, for example by inserting delivery means in a blood vessel to within a short distance from a site to be treated and at a branch or branches (preferably the most immediate) to a network of vessels carrying blood at the site and injecting the carrier through the delivery means, and establishing a magnetic field exterior to the body and adjacent to the site of sufficient field strength to guide a substantial quantity of the injected carrier to, and retain the substantial quantity of the carrier at, the site. Preferably, the magnetic field is of sufficient field strength to draw the carrier at the site adjacent to soft tissue of the network of vessels thus avoiding substantial embolization of any of the network of vessels.

It is therefore an object of this invention to provide an improved magnetically responsive carrier composition for carrying biologically active substances and methods of production and use thereof.

It is another object of this invention to provide a magnetically responsive carrier for biologically active substances which has improved magnetic responsiveness, is capable of greater absorption of the biologically active substance, and which is durable during storage and use.

It is another object of this invention to provide a magnetically responsive composition for carrying a biologically active substance comprising particles less than 5 μm in size, each particle including carbon and iron with the carbon distributed throughout the volume of each particle.

It is still another object of this invention to provide a composition utilized for localized in vivo treatment of disease including a carrier with particles between about 1 μm and 4 μm in size, each particle including carbon and iron with the carbon distributed throughout the volume of the particle, and a biologically active substance selected for its efficacy in treating the disease absorbed on the particles.

It is yet another object of this invention to provide a method of producing a magnetically responsive carrier composition including the step of jointly deforming a mechanical mixture of iron and carbon powders for a time sufficient to bind the powders into particles less than 5 μm in size, each particle including carbon and iron with the carbon distributed throughout the volume of each of the particles.

It is still another object of this invention to provide a method for producing a magnetically responsive composition for localized in vivo treatment of disease including the steps of providing a mixture of iron and carbon, mechanically processing the mixture sufficiently to bind the carbon and the iron into particles, a substantial portion of the particles including carbon and iron with the carbon distributed throughout the volume of each particle, separating the particles to select particles of a size of between about 1 μm and 4 μm from the substantial portion of the particles, and absorbing a biologically active substance onto the selected particles.

It is yet another object of this invention to provide a method for localized in vivo treatment of disease in a body comprising providing a magnetically responsive ferrocarbon carrier having a biologically active substance selected for its efficacy in treating the disease absorbed thereon, inserting delivery means in a blood vessel to within a short distance from a site to be treated and at a branch or branches to a network of vessels carrying blood at the site, injecting the carrier through the delivery means, and establishing a magnetic field exterior to the body and adjacent to the site of sufficient field strength to guide a substantial quantity of the injected carrier to, and retain the substantial quantity of the carrier at, the site and to draw the carrier at the site adjacent to soft tissue of the network of vessels thus avoiding substantial embolization of any of the network of vessels.

It is still another object of this invention to provide a method for localized in vivo treatment of disease in a body comprising absorbing a biologically active substance onto a magnetically responsive carrier composition including particles less than 5 μm in size, each particle including carbon and iron with the carbon distributed throughout the volume of each particle, injecting the carrier with the biologically active substance absorbed thereon into the body, and establishing a magnetic field exterior to the body and adjacent to a treatment site of sufficient field strength to guide a substantial quantity of the injected carrier to, and retain the substantial quantity of the carrier at, the site.

With these and other objects in view, which will become apparent to one skilled in the art as the description proceeds, this invention resides in the novel construction, combination, arrangement of parts and methods substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIG. 1 is a magnified photograph (12000×) of particles of the carrier composition of this invention;

FIG. 2a is a magnified photograph (30,000×) of a particle of the carrier composition of this invention;

FIG. 2b is a sectional illustration of the particle of FIG. 2a;

FIGS. 3a through 3h are illustrations of a tumor during periods of treatment utilizing drugs absorbed on the carrier composition and delivered to, and maintained at, the tumor site utilizing one method of this invention;

FIG. 4 is a diagram illustrating one example of application and magnetic targeting of the carrier composition; and FIG. 5 is a diagram illustrating the carrier composition (having a drug absorbed thereon) at a pathological structure.

DESCRIPTION OF THE INVENTION

The magnetically controllable, or guided, carrier composition of this invention comprises composite, volume-compounded ferrocarbon particles of 0.2 to 5.0 µm in size, and preferably between 1.0 and 4.0 µm, containing 1.0 to 95.0% by volume of carbon, and preferably between about 20 and 50% (about 40% carbon having been found to exhibit characteristics useful in many applications). The particles are produced by a joint deformation of a mechanical mixture of iron and carbon powders, after which the obtained particles are placed in a solution of a biologically active substance, the finished product then being separated (it being understood that separation could occur before exposure to the biologically active substance).

As shown in FIGS. 1 and 2a, ferrocarbon particles 8 manufactured by the method of this invention are of a generally spheroidal shape, with the inclusions of carbon deposits 10 being located throughout the whole volume of each particle (both at the surface and the interior of each particle). Uniform distribution of carbon 10 throughout the whole volume of each composite particle provides for a strong connection between the components (iron 12 and carbon 10) which is not broken during prolonged storage of the magnetically controlled composition, its transportation, strewing, packing and direct use.

The choice of the particles' size is determined in part by the constraints imposed by technological capabilities on producing particles under 0.2 µm. With regard to the preferred particle size range, for particles less than 1.0 µm carrying capacity is needlessly reduced. With particle sizes exceeding 4.0 µm an undesired degree of embolization of vessels becomes possible, coagulation of dispersion may take place (which makes injections more difficult) and the speed of discharging biologically active substances from the particles in the targeted pathological zones slows.

Regarding the justification for the chosen range of volume content of carbon in composite particles 8, while with carbon content less than 1.00% by volume specific absorption capacity of the magnetically controlled particles 8 (in dispersion) is enough for the transport of the required amount of biologically active substance towards the pathologic zone, it takes a greater quanity of the carrier, either by increased dosage or by increased number of injections, to reach the required concentration of biologically active substance in the damaged tissues. With carbon content exceeding 95.00% by volume, the susceptibility, or responsiveness, of composite particles 8 to a magnetic field decreases, and thus conditions for their control in the body worsen (although absorption capacity increases). In addition, the particles become rather friable at carbon content levels exceeding 95%, lacking in such case strong connection between the iron and carbon components, thus achieving less desirable technical characteristics and making their destruction (separation into constituent components) possible during storage and/or direct use.

The utilization of a method (such as is described below) which jointly deforms a mechanical mixture of iron and activated carbon powders enables achievement of a substantially uniform distribution of carbon throughout the volume of each composite particle, ensures their spheroidal form and achieves a share of 0.2 to 4.0 µm size composite particles of 50.00 to 95.00% or more of production volume.

Due to the fact that it is metallic (i.e., substantially elemental) iron and not its oxides (as is the case in previously known magnetically controlled dispersions) which is the ferromagnetic component in the produced composite particles of this invention, the magnetic susceptibility, or responsiveness, of ferrocarbon particles 8 is considerably higher.

In addition, intensive mechanical deformation and/or reintegration of iron particles 12 and the resulting formation within the particles of a well-developed substructure (see FIG. 2b), a connected network of iron forming a network of voids having carbon deposits 10 captured therein, which takes place during the process of joint deformation of the mechanical mixture of iron and carbon particles, also leads to an increase in the magnetic susceptibility of iron inclusions in ferrocarbon particles 8 as compared with non-deformed iron particles. Thus, the composite ferrocarbon particles produced by the herein suggested method have, for example, from 2.5 to 4.0 times greater magnetic susceptibility than the particles of the previously known magnetically controlled dispersion shown in European Patent Office Publication No. 0 451 299 A1, though ferromagnetic content in both is about the same. This improved responsiveness of ferrocarbon particles 8 makes it possible, in some cases, to decrease if desired the intensity of the magnetic field or fields utilized to guide the particles, and thereby lessen its effect on the human organism subjected to the therapy.

Because of a larger surface of carbon deposits 10 in particles 8 in comparison with other previously known ferrocarbon carriers described above, specific absorption capacity is increased (from about 2.5% of the absorbed biologically active substance out of the mass of a previously known magnetically controlled particle to up to about 7.5% in the case of particles 8; or, in different terms, from 25 mg of biologically active substance per gram of the previously known magnetically controlled dispersion up to about 75 mg of absorbed biologically active substance per gram of particles 8). This allows, in use, for injection of much less of the carrier to achieve a given dose of the biologically active substance or, alternatively, for higher dosage of the biologically active substance per injection over some previously known carriers.

The following describes a method of production of the carrier composition of this invention utilized to produce small quantities of the carrier, it being understood that other means and mechanisms could be conceived of for the joint deformation of iron and carbon powders which comprise the essential starting elements for production of the carrier. The procedure utilized exerts mechanical pressure on iron particles (normally spherical) to deform the iron particles and develop a substantial substructure which captures the carbon. It is felt that no molecular bonding is involved. The formation of the carrier particles is accomplished without the addition of heat in the process, and is conducted in the presence of a liquid, for example 96% ethanol, to inhibit oxidation of the iron and to assure that the carrier particles produced are clean (sterile). The liquid may also serve as a lubricant during the joint deformation of the iron and carbon particles, and it is felt that use of ethanol reduces compacting of carbon during processing resulting in less dense carbon deposits in the carrier composition, thereby providing greater absorption capacity.

For example, to produce carrier composition having a 60%/40% iron/carbon makeup, one part of substantially pure iron particles form 1 µm to 300 µm (preferable 2 µm to 10 µm) in size are mixed with 0.3 to 0.6 parts of substantially pure activated carbon granules (typically about 50 µm to 600 µm in size). The iron particles and carbon granules are mixed vigorously to achieve good distribution throughout the volume.

The mixture is put into a standard laboratory planetary ball, or attrition, mill of the type used in powdered metallurgy, for example having 6 mm diameter balls (any other device capable of mechanically processing the mixture to its desired state could be utilized), with a ball spacing adequate for deformation of the iron and carbon (and depending on the size of the particles of iron and granules of carbon initially, ball spacing being adjusted during milling until the space between balls is ultimately about 2 to 3 μm at the end of the process). A liquid (for example, by volume, 1 part ethanol to one part of the iron/carbon mixture initially) is added and the mixture is milled for between 4 and 12 hours (or for the time necessary to produce the particles as heretofore described) with liquid being added periodically to maintain wetness of the mixture. Depending on the mill used, the mill may be run at anywhere from 120 RPM to 1000 RPM, the process not being overly sensitive to the speed of the mill (it being felt that speeds over 1000 RPM could create an undesirable quantity of overly small particles).

After milling, the resulting particles are moved to a sterile environment (for example, an ultra-violet chamber) and are ambiently air dried (i.e., to evaporate the liquid).

By a combined process of magnetic selection and sieving (for example, blowing the particles through a 4 μm filter), the particles are separated to obtain particles of 1–4 microns in size which exhibit desired magnetic responsiveness. It has been found that, utilizing a carefully monitored milling process, typically less than 5% of production is not within the appropriate size range and/or is otherwise unusable. The particles are then sorted into dosages (typically one gram doses) and packaged, care being taken at each stage to maintain a sterile environment.

When ready for use (or, in the alternative, before packaging where a carrier is to be delivered with a preselected biologically active substance already absorbed thereon), up to 75 mg (50 mg is preferred to be absolutely assured of 100% absorption) of the biologically active substance in solution is added to 1 gram of the carrier. When ready for application to a patient, the combination is placed into suspension (for example, 5 to 10 ml) utilizing normal procedures.

Experimental evidence shows increased therapeutic efficiency of the use of the magnetically controlled carrier composition of this invention with an anti-tumorous preparation on a tumorous growth in comparison with previously known magnetically controlled dispersions.

Tests were carried out on male rats of the Vistor Line (bred at Stolbovaya Station of the USSR Academy of Medical Sciences). The rats were infused with carcinosarcoma Worker 256 under the tail's skin. When the tumorous volume averaged 986±98 mm³ the animals were divided into 4 groups, 10 rats in each. The first group (group I) was a control group, and groups II through IV where experimental ones.

The animals in group II were given intravenous injections of a water solution of rubomicine in the amount of 2 mg/kg during 5 days (the model of traditional use of such anti-cancerous preparations in clinics). The rats in group III were injected with a suspension of ferrocarbon dispersion produced by the previously known method described in European Patent Office Publication No. 0 451 299 A1. The dosage of ferrocarbon particles was 160 mg/kg, and the dosage of absorbed rubomicine thereon was 3.2 mg/kg. This suspension was injected into the tail vein after placing a permanent magnet with an intensity of the magnetic field of 6000 oersteds on the surface of the tumor. Magnetic localization of the magnetically controlled suspension in the tumorous growth zone was monitored by x-ray pictures.

The animals from group IV were given (using the same injection and magnetic control techniques, including placement of a permanent magnet with an intensity of the magnetic field of 600 oersteds on the surface of the tumor and x-ray monitoring) a one-time intravenous injection of the magnetically controlled dispersion produced in accord with the methods of this invention, the dosage being 160 mg/kg. The combination of components (iron/carbon) in each individual particle of the dispersion was 60/40, which was similar to the ratio in the dispersion produced by the previously known method used in experimental group III.

Due to the improved absorptive capability of particles 8, the dose of rubomicine absorbed on the magnetically controlled carrier particles of this invention was 9.96 mg/kg, which was 2.8 times more than the rubomicine absorbed by the previously known carrier particles in the experiment with the rats of group III. This result was achieved solely due to the relative specific absorption capacities of the given carriers.

Observation of the animals gave the following results. The life span of animals in control group I averaged 21±1.5 days. In group II, as a results of prescribed intravenous injections of the water solution of rubomicine (model of traditional use of antitumorous drugs), the rats' life span increased by an average of 4.5 days ($P<0.05$). The animals from experimental group III lived during 46±4.3 days, which was 2.2 times more ($P>0.001$) than the life span of control animals.

In group IV, 6 rats out of 10 (i.e., 60% of the cases) demonstrated complete dissolution of the tumor, which took place during 5 to 7 days after the one-time injection of the suspension of the magnetically controlled composition. Moreover, the remaining 4 rats from this group lived during 57.4±5.9 days, which exceeded the life span of the animals from group III by 25.0%, and is 2.7 times more as compared with the rats from control group I. The animals from group IV which showed complete regression of the tumors did not see any recurrence of tumorous growth during 157 days of observation which testifies to a complete elimination of the tumors in these rats.

Further clinical observation has documented the effectiveness of this invention. FIGS. 4 and 5 illustrate use of this invention for treatment and observation of a 61 year-old woman admitted on Feb. 13, 1992 to the Zil Hospital in Moscow, Russia (CIS) and diagnosed with cancer of the left mammary gland $T_3N_xM_x$.

The diagnosis was first made in 1989 when a biopsy was done. In December of 1991, focal radiation therapy (10 grey) resulted in the tumor being partially reduced. The decision was made to use the intra-arterial selective chemotherapy method of localized in vivo treatment of this invention utilizing the carrier of this invention with doxorubycin (Adriamycin) absorbed on the carrier.

Before the treatment, the dimensions of the tumor (illustrated in FIGS. 3a and 3b) were 44 mm×33 mm×37 mm (65 mm×45 mm, manual). On Feb. 24, 1992 a puncture of the femoral artery (FIG. 4) and injection of a vascular catheter into the aorta according to the Seldinger method were performed under local anaesthesia (0.5% novocaine, 30 ml). Under roentgenologic and contrast control, the catheter was placed at 25 mm distance from the branch to the left intra-pectoral artery (a. mammaria interna sinisra). A newly prepared suspension of gelatinol with ferrocarbon particles 8 having 15 mg doxorubycin (Adriamycin) absorbed thereon was injected through the catheter. At this time, a magnet having a magnetic field intensity of 15,000 oersteds was placed over the tumor. As a result, the injected suspension was localized and was kept by the magnetic field in the zone of the tumor for 20 minutes (a time sufficient for full microembolization of the tumor feeding capillaries). The patient's condition was satisfactory at the time of therapy.

As shown in FIGS. 3c and 3d, by Feb. 28, 1992 the patient's condition had improved, with an ultrasonic examination of the left mammary gland showing the dimensions of the tumor at 42 mm×33 mm×40 mm. The tumor had a legible contour. By Mar. 12, 1992, the dimensions of the tumor were found to have been reduced by 66.3% to 32 mm×27 mm×21 mm (FIGS. 3e and 3f), and by April 14 to have been reduced by 99.22% to 10 mm×6 mm×7 mm (FIGS. 3g and 3h).

It is felt that by releasing the carrier immediately upstream of the tumor (or other pathological) site, rather than penetrating the tumor, equally effective application of the biologically active substance occurs while potentially benefitting the patient by limiting spread of disease occasioned by puncture of the tumorous tissue. While a larger magnetic field was utilized in the above example of treatment, it has been found that the carrier composition of this invention begins to react in a field as small as 250 oersteds/cm (prior art carriers needing a field as large a 500 oersteds/cm before being influenced).

FIG. 5 illustrates what is believed to occur under magnetic control at the treatment site. Under the influence of the applied magnetic field, the carrier particles are induced into the capillary network feeding the tumor. The particles are drawn closely adjacent to the soft tissue of the lumen of the capillaries (or perhaps even into the soft tissue) thereby reducing or eliminating the potential for embolization of the vessels. The biologically active substance is released from the carrier particles by a dynamic process of replacement of the substance in the carrier by materials produced by the body (for example the necrotic products of the tumor itself), such as proteins, glucose, lipids, peptides, or the like, thus literally pushing the biologically active substance out of the carrier particles.

To replace the biologically active substance in the carrier particles, it is felt that the replacing substance must have a higher specific gravity than the biologically active substance, thus accounting for the low degree of washout of the biologically active substance in the blood stream (typically under 10%). Even fractions of the carrier not attracted to the treatment site by the magnetic field or escaping from the treatment site (typically around 10%) are effective, as these fractions remain active against tumor cells in the blood and elsewhere (metastasis reduction has been observed in some cases). Since the carrier composition is formed of material which is readily processed or metabolized by the body, all carrier particles are excreted or metabolized within 30 days of application.

As may be appreciated, an improved magnetically responsive carrier for biologically active substances and methods for producing and using the same are provided by this invention, particles forming the carrier exhibiting improved responsiveness to magnetic fields, having improved absorptive capacity, and being durable during storage and use.

What is claimed is:

1. A method for localized in vive treatment of disease comprising:

providing a magnetically responsive ferrocarbon carrier adapted to pass through a blood vessel to a disease site bearing therewith a biologically active substance selected for its efficacy in treating a disease;

inserting a delivery means into the blood vessel of a body being treated for the disease to within a short distance from the site to be treated;

injecting said carrier through said delivery means; and establishing a magnetic field exterior to the body and adjacent to said site of sufficient field strength to guide a portion of said carrier through the blood vessel to a point at or near the site so that a therapeutic amount of the biologically active substance contacts the disease site.

2. The method of claim 1 wherein the active substance is absorbed on the carrier.

3. The method of claim 1 wherein the biologically active substance is released from the carrier at the site by a process of replacement of the substance with a material having a higher specific gravity produced by the body.

4. The method of claim 3 wherein the material is blood, and replacement of the substance by blood is less than 30% by volume.

5. The method of claim 1, 2 or 3 further comprising the step that the carrier is removed from the body by excretion and metabolism.

6. The method of claim 5 wherein the carrier is fully removed within 30 days of its injection.

7. The method of claim 1, 2, 3 or 5 wherein the carrier includes particles containing iron and carbon, with the carbon being distributed substantially uniformly throughout the volume of the particles.

8. The method of claim 1, wherein the magnetic field established is as small as 250 oersteds/cm.

9. A method for localized in vivo treatment of disease comprising:

absorbing a biologically active substance onto a magnetically responsive carrier composition including particles less than about 5 µm in crossection, each particle containing carbon and iron with carbon distributed substantially uniformly throughout the volume of the particle;

injecting the carrier with the absorbed biologically active substance thereon into a body having a disease site;

establishing a magnetic field exterior to the body and adjacent to the site, wherein the magnetic field is of sufficient field strength to guide and retain at the site a portion of the carrier; and releasing a therapeutic amount of the active substance from the carrier so as to contact the site.

10. The method of claim 9 wherein the field strength of the established magnetic field is as low as 250 oersteds/cm.

11. The method of claim 9 or 10 wherein the amount of absorbed active substance is in excess of 2.5% by mass of the carrier.

12. The method of claim 9 or 10 wherein the amount of absorbed active substance is in excess of 7.5% by weight of the carrier.

13. The method of claim 9 wherein the carrier is guided to soft tissue adjacent a network of blood vessels at the treatment site, thus avoiding substantial emboliization of any of the network of vessels.

* * * * *

UNITED STATES PATENT AND TRADEMARK OFFICE
CERTIFICATE OF CORRECTION

PATENT NO. : 5,705,195
DATED : January 6, 1998
INVENTOR(S) : Viktor A. Volkonsky, et al.

It is certified that error appears in the above-identified patent and that said Letters Patent is hereby corrected as shown below:

Claim 1, line 1, change "vive" to -- vivo --.

Signed and Sealed this

Twenty-fourth Day of March, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,705,195
DATED : 01/06/98
INVENTOR(S) : VIKTOR A. VOLKONSKY et al.

It is certified that error appears in the above-identified patent and that said Letters Patent is hereby corrected as shown below:

Col. 8, Line 44: correct "$T_3N_xM_x$" to "$T_3N_1M_1$"

Signed and Sealed this

Twenty-ninth Day of February, 2000

*Attest:*

Q. TODD DICKINSON

*Attesting Officer*   *Commissioner of Patents and Trademarks*